(12) United States Patent
Hogwood et al.

(10) Patent No.: US 10,750,785 B2
(45) Date of Patent: Aug. 25, 2020

(54) AEROSOL-GENERATING SYSTEM COMPRISING A BIMETALLIC STRIP

(71) Applicant: Philip Morris Products S.A., Neuchatel (CH)

(72) Inventors: Jonathan Hogwood, Royston (GB); Stuart Michael Ruan Jones, Royston (GB); John Antony Stephenson, Cambridge (GB); David Edington, St. Albans (GB); Christopher Coulson, London (GB)

(73) Assignee: Philip Morris Products S.A., Neuchatel (CH)

(*) Notice: Subject to any disclaimer, the term of this patent is extended or adjusted under 35 U.S.C. 154(b) by 334 days.

(21) Appl. No.: 15/555,717

(22) PCT Filed: Mar. 24, 2016

(86) PCT No.: PCT/EP2016/056574
§ 371 (c)(1),
(2) Date: Sep. 5, 2017

(87) PCT Pub. No.: WO2016/156213
PCT Pub. Date: Oct. 6, 2016

(65) Prior Publication Data
US 2018/0042304 A1 Feb. 15, 2018

(30) Foreign Application Priority Data
Mar. 27, 2015 (EP) .................. 15161537

(51) Int. Cl.
*A24F 47/00* (2020.01)
*A61M 15/06* (2006.01)
(52) U.S. Cl.
CPC .......... *A24F 47/008* (2013.01); *A61M 15/06* (2013.01); *A61M 2205/3368* (2013.01)

(58) Field of Classification Search
CPC ...... A24F 47/008; A24F 47/00; A24F 47/002; A24F 47/004; A24F 47/006; A61M 15/06;
(Continued)

(56) References Cited

U.S. PATENT DOCUMENTS 9,974,329 B2   5/2018  Buehler
9,999,247 B2   6/2018  Ruscio
(Continued)

FOREIGN PATENT DOCUMENTS

CN   101626700 A   1/2010
CN   101951796 A   1/2011
(Continued)

OTHER PUBLICATIONS

International Search Report and Written Opinion dated Jun. 10, 2016 in PCT/EP2016/056574, filed Mar. 24, 2016.
(Continued)

*Primary Examiner* — Timothy A Stanis
*Assistant Examiner* — Arielle Wolff
(74) *Attorney, Agent, or Firm* — Oblon, McClelland, Maier & Neustadt, L.L.P.

(57) ABSTRACT

An aerosol-generating system is provided, including an aerosol-generating device including a heater element; an aerosol-generating article including a medicament source and a volatile delivery enhancing compound source; a bimetallic strip provided in the aerosol-generating device or the aerosol-generating article, the bimetallic strip including a first end in thermal contact with the heater element and a second end in thermal contact with the volatile delivery enhancing compound source, the bimetallic strip being configured so that heating the first end of the bimetallic strip
(Continued)

above a predetermined temperature results in displacement of the first end of the bimetallic strip away from the heater element.

11 Claims, 1 Drawing Sheet

(58) Field of Classification Search
CPC .......... A61M 2205/3368; A61M 15/05; A61M 11/04; A61M 11/041; A61M 11/042; A61M 11/043; A61M 11/044; A61M 11/045; A61M 11/046; A61M 11/047; A61M 11/048; H05B 1/0244
See application file for complete search history.

(56) References Cited

U.S. PATENT DOCUMENTS

| | | | |
|---|---|---|---|
| 10,085,482 B2 * | 10/2018 | Silvestrini | A24B 15/16 |
| 2007/0283972 A1 | 12/2007 | Monsees et al. | |
| 2008/0241255 A1 | 10/2008 | Rose | |
| 2008/0276947 A1 | 11/2008 | Martzel | |
| 2009/0151717 A1 | 6/2009 | Bowen et al. | |
| 2009/0260641 A1 | 10/2009 | Monsees et al. | |
| 2009/0260642 A1 | 10/2009 | Monsees et al. | |
| 2009/0293892 A1 | 12/2009 | Williams | |
| 2014/0000638 A1 | 1/2014 | Sebastian et al. | |
| 2014/0261488 A1 | 9/2014 | Tucker | |
| 2014/0366898 A1 | 12/2014 | Monsees | |
| 2015/0150308 A1 | 6/2015 | Monsees et al. | |
| 2015/0157056 A1 | 6/2015 | Bowen et al. | |
| 2016/0022930 A1 | 1/2016 | Greim | |
| 2016/0081395 A1 * | 3/2016 | Thorens | A61M 11/042 128/202.21 |
| 2017/0303581 A1 | 10/2017 | Schaller | |
| 2017/0347706 A1 | 12/2017 | Aoun | |
| 2018/0104425 A1 * | 4/2018 | Hogwood | A61M 15/06 |

FOREIGN PATENT DOCUMENTS

| | | |
|---|---|---|
| CN | 102014995 A | 4/2011 |
| CN | 104114049 A | 10/2014 |
| JP | 2009-502136 A | 1/2009 |
| JP | 2009-521940 A | 6/2009 |
| JP | 2011-505874 A | 3/2011 |
| WO | WO 2007/012007 A2 | 1/2007 |
| WO | WO 2008/12160 A1 | 10/2008 |
| WO | WO 2011/034723 A1 | 3/2011 |
| WO | WO 2013/040193 A2 | 3/2013 |
| WO | WO 2014/004648 A1 | 1/2014 |
| WO | WO 2014/140320 A1 | 9/2014 |
| WO | WO 2014/187770 A2 | 11/2014 |
| WO | WO 2015/082652 A1 | 6/2015 |

OTHER PUBLICATIONS

Combined Chinese Office Action and Search Report dated Sep. 16, 2019 in Chinese Patent Application No. 201680015136.7 (with English translation), 10 pages.
Combined Chinese Office Action and Search Report dated Dec. 3, 2019, in Patent Application No. 201680016624.X (with English translation), 11 pages.
International Search Report and Written Opinion dated Jun. 14, 2016 in PCT/EP2016/056579, filed Mar. 24, 2016.
U.S. Office Action dated Nov. 29, 2019 in corresponding U.S. Appl. No. 15/559,480 (21 pages).
Extended European Search Report dated Sep. 10, 2015 in Patent Application No. 15161529.1 (4 pages).
Notice of Allowance dated Apr. 6, 2020 in Japanese Patent Application No. 2017-545955 (with English translation), 4 pages.

* cited by examiner

AEROSOL-GENERATING SYSTEM COMPRISING A BIMETALLIC STRIP

The present invention relates to an aerosol-generating system for generating an aerosol comprising a medicament. The invention finds particular application as an aerosol-generating system for generating an aerosol comprising nicotine salt particles.

Some devices for delivering nicotine or other medicaments to a user comprise a volatile acid, such as pyruvic acid, or other volatile delivery enhancing compound source and a nicotine or other medicament source. The volatile delivery enhancing compound is reacted with nicotine in the gas phase to form an aerosol of nicotine salt particles that is inhaled by the user.

At room temperature pyruvic acid and nicotine are both sufficiently volatile to form respective vapours that react with one another in the gas phase to form nicotine pyruvate salt particles. However, the vapour pressure of pyruvic acid at room temperature is substantially greater than that of nicotine leading to a difference in the vapour concentration of the two reactants. Differences between the vapour concentration of the volatile delivery enhancing compound and nicotine in devices can disadvantageously lead to the delivery of unreacted delivery enhancing compound vapour to a user.

In devices comprising a nicotine or other medicament source and a volatile delivery enhancing compound source it would be desirable to produce a maximum quantity of medicament salt particles for delivery to a user using a minimum quantity of reactants. Consequently, it would be desirable to provide an aerosol-generating system in which the quantity of unreacted volatile delivery enhancing agent is minimised.

The present invention provides an aerosol-generating system comprising an aerosol-generating device comprising a heater element, and an aerosol-generating article. The aerosol-generating article comprises a medicament source and a volatile delivery enhancing compound source. The aerosol-generating system further comprises a bimetallic strip provided in the aerosol-generating device or the aerosol-generating article, the bimetallic strip comprising a first end in thermal contact with the heater element and a second end in thermal contact with the volatile delivery enhancing compound source. The bimetallic strip is configured so that heating the first end of the bimetallic strip above a predetermined temperature results in displacement of the first end of the bimetallic strip away from the heater element.

The present invention also provides use of a bimetallic strip to control heating of a volatile delivery enhancing compound source in an aerosol-generating system comprising a medicament source and the volatile delivery enhancing compound source.

As used herein, the term "aerosol-generating device" refers to a device that interacts with an aerosol-generating article to generate an aerosol that is directly inhalable into a user's lungs thorough the user's mouth.

As used herein, the term "aerosol-generating article" refers to an article comprising an aerosol-forming substrate capable of releasing volatile compounds, which can form an aerosol. In certain embodiments, the aerosol-generating article may comprise an aerosol-forming substrate capable of releasing upon heating volatile compounds, which can form an aerosol. An aerosol-generating article may be entirely consumable and mainly comprise a medicament source and a volatile delivery enhancing compound. Alternatively, an aerosol-generating article may comprise a reusable portion, such as a mouthpiece configured for attachment to an aerosol-generating device, and a consumable portion comprising the medicament and volatile delivery enhancing compound sources and configured for insertion into the reusable portion.

As used herein, the term "aerosol-generating system" refers to a combination of an aerosol-generating article with an aerosol-generating device.

As used herein, the term "medicament source" refers to a source of one or more volatile compounds intended for delivery to the lungs of a user. Preferably, the medicament source comprises a nicotine source.

As used herein, the term "volatile delivery enhancing compound source" refers to a source of one or more volatile compounds that react with the medicament source in the gas phase to aid delivery of the one or more compounds from the medicament source to the user.

As used herein, the term "thermal contact" refers to two components arranged so that heat can transfer conductively between the two components. The two components may contact each other directly, or one or more thermally conductive elements may be provided between the first and second components so that heat is conducted between the first and second components via the one or more thermally conductive elements.

By providing a bimetallic strip extending between the heater element and the volatile delivery enhancing compound source, an aerosol-generating system in accordance with the present invention advantageously allows precise and self-regulating control of the maximum temperature to which the volatile delivery enhancing compound source is heated. Advantageously, the temperature control is independent of the maximum temperature to which the heater element is heated. Therefore, in an aerosol-generating system according to the present invention, the heater element can be used to heat other components, such as the medicament source, to a higher temperature than the volatile delivery enhancing compound source. An aerosol-generating system in accordance with the present invention can therefore allow precise control of the amount of volatile delivery enhancing compound vapour and medicament vapour released from the volatile delivery enhancing compound source and the medicament source respectively. This advantageously enables the vapour concentrations of the volatile delivery enhancing compound and the medicament to be controlled and balanced proportionally to yield an efficient reaction stoichiometry. This advantageously improves the efficiency of the formation of an aerosol and the consistency of the medicament delivery to a user. It also advantageously reduces the delivery of unreacted delivery enhancing compound vapour and unreacted medicament vapour to a user.

The first end of the bimetallic strip may be in direct contact with the heater element. The first end of the bimetallic strip may contact the heater element via one or more intervening thermally conductive components. The bimetallic strip may be configured so that when the first end of the bimetallic strip is heated above the predetermined temperature the first end of the bimetallic strip is displaced away from the one or more intervening thermally conductive components, or the bimetallic strip and the one or more intervening thermally conductive components are both displaced away from the heater element if the one or more thermally conductive components are secured to the first end of the bimetallic strip.

The second end of the bimetallic strip may be in direct contact with the volatile delivery enhancing compound source. The second end of the bimetallic strip may contact the volatile delivery enhancing compound source via one or more intervening thermally conductive components.

The bimetallic strip may comprise a simple linear bimetallic strip forming a cantilever having a first moveable end in thermal contact with the heater element and a second fixed end in thermal contact with the volatile delivery enhancing compound source. Alternatively, the bimetallic strip may be formed into a more complex shape, such as a bimetallic spiral or helix. In this case, the first end of the bimetallic strip forms a first end of the helix and the second end of the bimetallic strip forms a second end of the helix. The particular shape of the bimetallic strip may be selected depending on the particular thermostatic control required to provide the desired heating of the volatile delivery enhancing compound source. In particular, the choice of metals in combination with the shape of the bimetallic strip can provide a desired speed of response, size of movement and thermal power transfer of the bimetallic strip.

The bimetallic strip is preferably formed from two layers of metal or metal alloy having different coefficients of thermal expansion. The two layers may be joined together by any suitable conventional process, such as cladding. Suitable metals for forming the first and second layers include aluminium, aluminium alloys, beryllium alloys, bismuth, brass, bronze, cadmium, cobalt alloys, copper, copper-nickel alloys, gold, iron, lead, magnesium, magnesium alloys, monel, nickel, nickel alloys, nickel aluminides, niobium, niobium alloys, palladium, platinum, rhenium, silver, silver alloys, steel, tantalum, tantalum alloys, tin, tin alloys, titanium, titanium aluminides, uranium, vanadium alloys, zinc, zinc alloys, and zirconium. In a preferred embodiment, the bimetallic strip comprises a first metallic layer comprising steel and a second metallic layer comprising copper or brass.

To accommodate thermal losses along the length of the bimetallic strip, the bimetallic strip may be configured to mechanically displace the first end of the bimetallic strip away from the heater element when the first end of the bimetallic strip is heated to a temperature that is higher than the desired temperature of the volatile delivery enhancing compound source. The bimetallic strip may be configured to mechanically displace the first end of the bimetallic strip away from the heater element when the first end of the bimetallic strip is heated to a temperature of at least about 300 degrees Celsius.

To reduce convective and radiative heating of the volatile delivery enhancing compound source, the volatile delivery enhancing compound source is preferably positioned downstream of the heater element. In such embodiments, the bimetallic strip extends between the heater element and the volatile delivery enhancing compound source. Reducing convective and radiative heating of the volatile delivery enhancing compound ensures that the temperature of the volatile delivery enhancing compound source can be precisely controlled using the bimetallic strip.

As discussed above, in some cases it is desirable to heat the medicament source to a different temperature than the volatile delivery enhancing compound source. The aerosol-generating system may be configured to heat the medicament source and the volatile delivery enhancing compound source of the aerosol-generating article so that the medicament source has a higher temperature than the volatile delivery enhancing compound source. The aerosol-generating system may be configured to heat the medicament source and the volatile delivery enhancing compound source of the aerosol-generating article so that the medicament source has a lower temperature than the volatile delivery enhancing compound source.

The medicament source may directly contact the heater element.

The aerosol-generating device and the aerosol-generating article may be configured to heat the medicament source to a first temperature and to heat the volatile delivery enhancing compound source to a second temperature, wherein the first temperature is at least about 50 degrees Celsius higher than the second temperature, preferably at least about 70 degrees Celsius higher than the second temperature, most preferably at least about 80 degrees Celsius higher than the second temperature. Additionally, or alternatively, the first temperature is preferably no more than about 100 degrees Celsius higher than the second temperature. Preferably, the temperature difference between the first and second temperatures is between about 50 and about 100 degrees Celsius, more preferably between about 60 and about 100 degrees Celsius, most preferably between about 80 and about 100 degrees Celsius.

In any of the embodiments described above, the aerosol-generating device and the aerosol-generating article may be configured to heat the volatile delivery enhancing compound source to a temperature of at least about 30 degrees Celsius. Additionally, or alternatively, the aerosol-generating device and the aerosol-generating article may be configured to heat the volatile delivery enhancing compound source to a temperature of less than about 100 degrees Celsius, preferably less than about 70 degrees Celsius. Preferably, the aerosol-generating device and the aerosol-generating article are configured to heat the volatile delivery enhancing compound source to a temperature of between about 30 and about 100 degrees Celsius, more preferably between about 30 and about 70 degrees Celsius.

In any of the embodiments described above, the aerosol-generating device and the aerosol-generating article may be configured to heat the medicament source to a temperature of at least about 50 degrees Celsius. Additionally, or alternatively, the aerosol-generating device and the aerosol-generating article may be configured to heat the medicament source to a temperature of less than about 150 degrees Celsius, preferably less than about 100 degrees Celsius. Preferably, the aerosol-generating device and the aerosol-generating article are configured to heat the medicament source to a temperature of between about 50 and about 150 degrees Celsius, more preferably between about 50 and about 100 degrees Celsius.

The medicament source of the aerosol-generating article may be sealed by one or more frangible barriers. The volatile delivery enhancing compound source of the aerosol-generating article may be sealed by one or more frangible barriers. Preferably, both sources are sealed by one or more frangible barriers.

The one or more frangible barriers may be formed from any suitable material. For example, the one or more frangible barriers may be formed from a metal foil or film.

At least one of the aerosol-generating device and the aerosol-generating article preferably further comprises a rupturing member positioned for breaking the one or more frangible barriers sealing one or both of the medicament and volatile delivery enhancing compound sources of the aerosol-generating article.

The medicament source and the volatile delivery enhancing compound source are preferably arranged in series within the aerosol-generating article.

As used herein, by "series" it is meant that the medicament source and the volatile delivery enhancing compound source are arranged within the aerosol-generating article so that in use an air stream drawn through the aerosol-generating article passes through one of the medicament source and the volatile delivery enhancing compound source and then passes through the other of the medicament source and the volatile delivery enhancing compound source.

The medicament source and the volatile delivery enhancing compound source may be arranged in parallel within the aerosol-generating article.

Preferably, the medicament source is upstream of the volatile delivery enhancing compound source so that in use medicament vapour is released from the medicament source into the air stream drawn through the aerosol-generating article and volatile delivery enhancing compound vapour is released from the volatile delivery enhancing compound source into the medicament-containing air stream drawn through the aerosol-generating article. The medicament vapour reacts with the volatile delivery enhancing compound vapour in the gas phase to form an aerosol, which is delivered to a user.

The volatile delivery enhancing compound preferably has a vapour pressure of at least about 20 Pa, more preferably at least about 50 Pa, more preferably at least about 75 Pa, most preferably at least 100 Pa. Unless otherwise stated, all vapour pressures referred to herein are vapour pressures at 25° C. measured in accordance with ASTM E1194-07.

Preferably, the volatile delivery enhancing compound has a vapour pressure of less than or equal to about 400 Pa, more preferably less than or equal to about 300 Pa, even more preferably less than or equal to about 275 Pa, most preferably less than or equal to about 250 Pa at 25° C.

The volatile delivery enhancing compound may have a vapour pressure of between about 20 Pa and about 400 Pa, more preferably between about 20 Pa and about 300 Pa, even more preferably between about 20 Pa and about 275 Pa, most preferably between about 20 Pa and about 250 Pa at 25° C.

The volatile delivery enhancing compound may have a vapour pressure of between about 50 Pa and about 400 Pa, more preferably between about 50 Pa and about 300 Pa, even more preferably between about 50 Pa and about 275 Pa, most preferably between about 50 Pa and about 250 Pa at 25° C.

The volatile delivery enhancing compound may have a vapour pressure of between about 75 Pa and about 400 Pa, more preferably between about 75 Pa and about 300 Pa, even more preferably between about 75 Pa and about 275 Pa, most preferably between about 75 Pa and about 250 Pa at 25° C.

The volatile delivery enhancing compound may have a vapour pressure of between about 100 Pa and about 400 Pa, more preferably between about 100 Pa and about 300 Pa, even more preferably between about 100 Pa and about 275 Pa, most preferably between about 100 Pa and about 250 Pa at 25° C.

The volatile delivery enhancing compound may comprise a single compound. The volatile delivery enhancing compound may comprise two or more different compounds.

Where the volatile delivery enhancing compound comprises two or more different compounds, the two or more different compounds in combination may have a vapour pressure of at least about 20 Pa at 25° C.

Preferably, the volatile delivery enhancing compound is a volatile liquid.

The volatile delivery enhancing compound may comprise a mixture of two or more different liquid compounds.

The volatile delivery enhancing compound may comprise an aqueous solution of one or more compounds. The volatile delivery enhancing compound may comprise a non-aqueous solution of one or more compounds.

The volatile delivery enhancing compound may comprise two or more different volatile compounds. The volatile delivery enhancing compound may comprise a mixture of two or more different volatile liquid compounds.

The volatile delivery enhancing compound may comprise one or more non-volatile compounds and one or more volatile compounds. The volatile delivery enhancing compound may comprise a solution of one or more non-volatile compounds in a volatile solvent or a mixture of one or more non-volatile liquid compounds and one or more volatile liquid compounds.

The volatile delivery enhancing compound may comprise an acid. The volatile delivery enhancing compound may comprise an organic acid or an inorganic acid. Preferably, the volatile delivery enhancing compound comprises an organic acid, more preferably a carboxylic acid, most preferably an alpha-keto or 2-oxo acid. The volatile delivery enhancing compound may comprise lactic acid. Other suitable acids includes aspartic acid, glutamic acid, salicylic acid, tartaric acid, gallic acid, levulinic acid, acetic acid, malic acid, citric acid, oxalic acid, sulphuric acid, palmitic acid, and alginic acid.

Preferably, the volatile delivery enhancing compound comprises an acid selected from the group consisting of 3-methyl-2-oxopentanoic acid, pyruvic acid, 2-oxopentanoic acid, 4-methyl-2-oxopentanoic acid, 3-methyl-2-oxobutanoic acid, 2-oxooctanoic acid and combinations thereof. Preferably, the volatile delivery enhancing compound comprises pyruvic acid.

Preferably, the volatile delivery enhancing compound source comprises a sorption element and a volatile delivery enhancing compound sorbed on the sorption element. The volatile delivery enhancing compound may be sorbed onto the sorption element during manufacture and the sorption element may be sealed. Alternatively, the volatile delivery enhancing compound may be stored separately from the sorption element, for example in a blister on or adjacent the sorption element. In such embodiments, the volatile delivery enhancing compound source is formed when the volatile delivery enhancing compound is released and sorbed onto the sorption element.

As used herein, by "sorbed" it is meant that the volatile delivery enhancing compound is adsorbed on the surface of the sorption element, or absorbed in the sorption element, or both adsorbed on and absorbed in the sorption element. Preferably, the volatile delivery enhancing compound is adsorbed on the sorption element.

The sorption element may be formed from any suitable material or combination of materials. For example, the sorption element may comprise one or more of glass, stainless steel, aluminium, polyethylene (PE), polypropylene, polyethylene terephthalate (PET), polybutylene terephthalate (PBT), polytetrafluoroethylene (PTFE), expanded polytetrafluoroethylene (ePTFE), and BAREX®.

Preferably, the sorption element is a porous sorption element.

For example, the sorption element may be a porous sorption element comprising one or more materials selected from the group consisting of porous plastic materials, porous polymer fibres and porous glass fibres.

The sorption element is preferably chemically inert with respect to the volatile delivery enhancing compound.

The sorption element may have any suitable size and shape.

The size, shape and composition of the sorption element may be chosen to allow a desired amount of volatile delivery enhancing compound to be sorbed on the sorption element.

Preferably, between about 20 μl and about 200 μl, more preferably between about 40 μl and about 150 μl, most preferably between about 50 μl and about 100 μl of the volatile delivery enhancing compound is sorbed on the sorption element.

The sorption element advantageously acts as a reservoir for the volatile delivery enhancing compound.

Preferably, the medicament has a melting point below about 150 degrees Celsius.

Preferably the medicament has a boiling point below about 300 degrees Celsius.

Preferably, the medicament comprises one or more aliphatic or aromatic, saturated or unsaturated nitrogenous bases (nitrogen containing alkaline compounds) in which a nitrogen atom is present in a heterocyclic ring or in an acyclic chain (substitution).

The medicament may comprise one or more compounds selected from the group consisting of: nicotine; 7-Hydroxymitragynine; Arecoline; Atropine; Bupropion; Cathine (D-norpseudoephedrine); Chlorpheneramine; Dibucaine; Dimemorphan, Dimethyltryptamine, Diphenhydramine, Ephedrine, Hordenine, Hyoscyamine, Isoarecoline, Levorphanol, Lobeline, Mesembrine, Mitragynine, Muscatine, Procaine, Pseudo ephedrine, Pyrilamine, Raclopride, Ritodrine, Scopolamine, Sparteine (Lupinidine) and Ticlopidine; tobacco smoke constituents, such as 1,2,3,4 Tetrahydroisoquinolines, Anabasine, Anatabine, Cotinine, Myosmine, Nicotrine, Norcotinine, and Nornicotine; anti-asthmatic drugs, such as Orciprenaline, Propranolol and Terbutaline; anti-angina drugs, such as Nicorandil, Oxprenolol and Verapamil; antiarrythmic drugs, such as Lidocaine; nicotinic agonists, such as Epibatidine, 5-(2R)-azetidinylmethoxy)-2-chloropyridine (ABT-594), (S)-3-methyl-5-(1-methyl-2-pyrrolidinyl)isoxazole (ABT 418) and (±)-2-(3-Pyridinyl)-I-azabicyclo[2.2.2]octane (RJR-2429); nicotinic antagonists, such as Methyllycacotinine and Mecamylamine; acetyl cholinesterase inhibitors, such as Galantamine, Pyridostigmine, Physostigmine and Tacrine; and MAO-inhibitors, such as Methoxy-N,N-dimethyltryptamine, 5-methoxy-α-methyltryptamine, Alpha-methyltryptamine, Iproclozide, Iproniazide, Isocarboxazide, Linezolid, Meclobemide, N,N-Dimethyltryptamine, Phenelzine, Phenyl ethylamine, Toloxatone, Tranylcypromine and Tryptamine.

Preferably, the medicament source comprises a nicotine source. The nicotine source may comprise one or more of nicotine, nicotine base, a nicotine salt, such as nicotine-HCl, nicotine-bitartrate, or nicotine-tartrate, or a nicotine derivative.

The nicotine source may comprise natural nicotine or synthetic nicotine.

The nicotine source may comprise pure nicotine, a solution of nicotine in an aqueous or non-aqueous solvent or a liquid tobacco extract.

The nicotine source may further comprise an electrolyte forming compound. The electrolyte forming compound may be selected from the group consisting of alkali metal hydroxides, alkali metal oxides, alkali metal salts, alkaline earth metal oxides, alkaline earth metal hydroxides and combinations thereof.

The nicotine source may comprise an electrolyte forming compound selected from the group consisting of potassium hydroxide, sodium hydroxide, lithium oxide, barium oxide, potassium chloride, sodium chloride, sodium carbonate, sodium citrate, ammonium sulfate and combinations thereof The nicotine source may comprise an aqueous solution of nicotine, nicotine base, a nicotine salt or a nicotine derivative and an electrolyte forming compound.

The nicotine source may further comprise other components including, but not limited to, natural flavours, artificial flavours and antioxidants.

The medicament source may comprise a sorption element as described above and a medicament sorbed on the sorption element. The medicament may be sorbed onto the sorption element during manufacture and the sorption element may be sealed. Alternatively, the medicament may be stored separately from the sorption element, for example in a blister on or adjacent the sorption element. In such embodiments, the medicament source is formed when the medicament is released and sorbed onto the sorption element.

The aerosol-generating device may be configured to heat the medicament source and the volatile delivery enhancing compound source of the aerosol-generating article so that the medicament source of the aerosol-generating article has a higher temperature than the volatile delivery enhancing compound source of the aerosol-generating article. The aerosol-generating device may be configured to substantially simultaneously heat the medicament source and the volatile delivery enhancing compound source of the aerosol-generating article.

The aerosol-generating device may further comprise a controller configured to control a supply of power to the heater element.

The aerosol-generating device may further comprise a power supply for supplying power to the heater element and a controller configured to control a supply of power from the power supply to the heater element. The controller of the aerosol-generating device may be configured to control a supply of power from an external power supply to the heater element.

The heater element may be an electric heater element powered by an electric power supply. Where the heater element is an electric heater element, the aerosol-generating device may further comprise an electric power supply and a controller comprising electronic circuitry configured to control the supply of electric power from the electric power supply to the electric heater element.

The power supply may be a DC voltage source. Preferably, the power supply is a battery. The power supply may be a Nickel-metal hydride battery, a Nickel cadmium battery, or a Lithium based battery, for example a Lithium-Cobalt, a Lithium-Iron-Phosphate or a Lithium-Polymer battery. The power supply may be another form of charge storage device such as a capacitor. The power supply may require recharging and may have a capacity that allows for the storage of enough energy for use of the aerosol-generating device with one or more aerosol-generating articles.

The heater element may be a non-electric heater, such as a chemical heating means.

The heater element of the aerosol-generating device preferably comprises a single heater element to simplify the construction of the aerosol-generating device. Differential heating of the medicament source and the volatile delivery enhancing compound source may be achieved by contacting at least one of the sources with the resilient member, which in turn is biased against the heater element.

The heater element may have any suitable shape. Preferably, the heater element is an elongate heater element. Preferably, the elongate heater element has a width that is greater than the thickness of the heater element so that the heater element forms a heater blade.

Preferably, the heater element is heated electrically. However, other heating schemes may be used to heat the heater element. The heater element may be heated by conduction from another heat source. The heater element may comprise an infra-red heater element, a photonic source, or an inductive heater element.

The heater element may comprise a heat sink, or heat reservoir comprising a material capable of absorbing and storing heat and subsequently releasing the heat over time to the aerosol-forming article. The heat sink may be formed of any suitable material, such as a suitable metal or ceramic material. Preferably, the material has a high heat capacity (sensible heat storage material), or is a material capable of absorbing and subsequently releasing heat via a reversible process, such as a high temperature phase change. Suitable sensible heat storage materials include silica gel, alumina, carbon, glass mat, glass fibre, minerals, a metal or alloy such as aluminium, silver or lead, and a cellulose material such as paper. Other suitable materials which release heat via a reversible phase change include paraffin, sodium acetate, naphthalene, wax, polyethylene oxide, a metal, a metal salt, a mixture of eutectic salts or an alloy.

The heater element preferably comprises an electrically resistive material. The heater element may comprise a non-elastic material, for example a ceramic sintered material, such as alumina ($Al_2O_3$) and silicon nitride ($Si_3N_4$), or printed circuit board or silicon rubber. Alternatively, the heater element may comprise an elastic, metallic material, for example an iron alloy or a nickel-chromium alloy.

Other suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, nickel-, cobalt-, chromium-, aluminium-titanium-zirconium-, hafnium-, niobium-, molybdenum-, tantalum-, tungsten-, tin-, gallium- and manganese-alloys, and super-alloys based on nickel, iron, cobalt, stainless steel, Timetal® and iron-manganese-aluminium based alloys. Timetal® is a registered trade mark of Titanium Metals Corporation, 1999 Broadway Suite 4300, Denver, Colo. In composite materials, the electrically resistive material may optionally be embedded in, encapsulated or coated with an insulating material or vice-versa, depending on the kinetics of energy transfer and the external physico-chemical properties required.

The aerosol-generating device may comprise one or more temperature sensors configured to sense the temperature of at least one of the heater element, the medicament source and the volatile delivery enhancing compound source. In such embodiments, the controller may be configured to control a supply of power to the heater element based on the sensed temperature.

The heater element may be formed using a metal having a defined relationship between temperature and resistivity. The metal may be formed as a track between two layers of suitable insulating materials. A heater element formed in this manner may be used both as a heater and a temperature sensor.

The invention will now be further described, by way of example only, with reference to the accompanying drawings in which.

Figure 1:
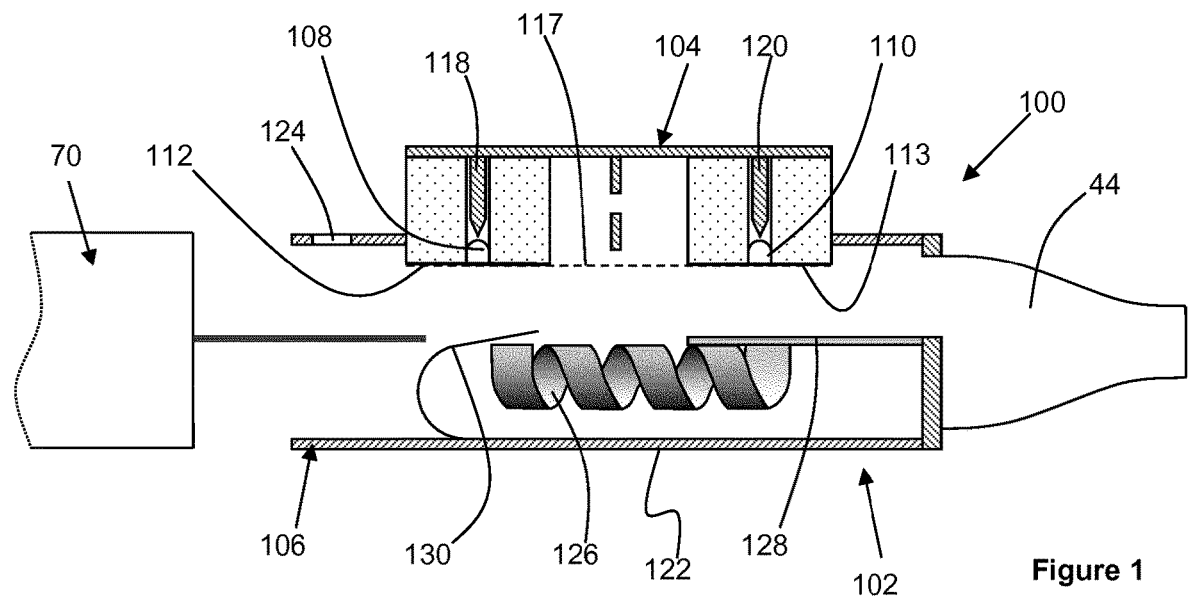
FIG. 1 shows an aerosol-generating system in accordance with an embodiment of the present invention, before activation of the aerosol-generating article and before full insertion of the aerosol-generating device into the aerosol-generating article.
Figure 2:
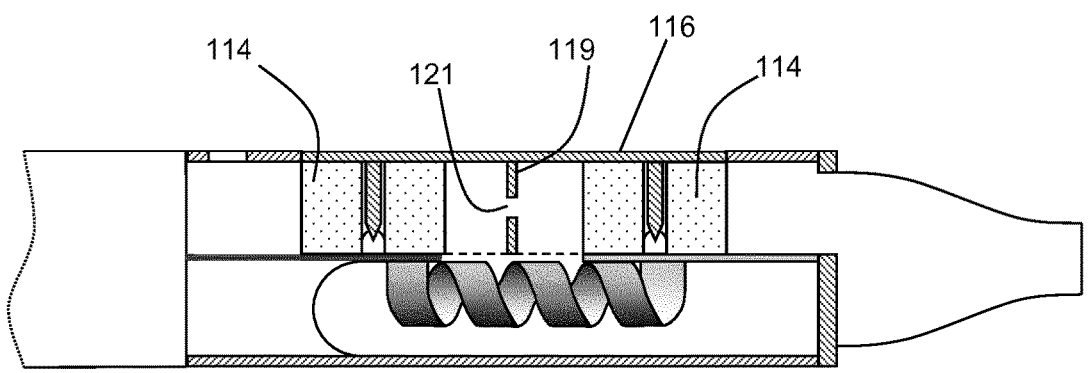
FIG. 2 shows the aerosol-generating system of FIG. 1 after activation of the aerosol-generating article and after full insertion of the aerosol-generating device into the aerosol-generating article.
Figure 3:
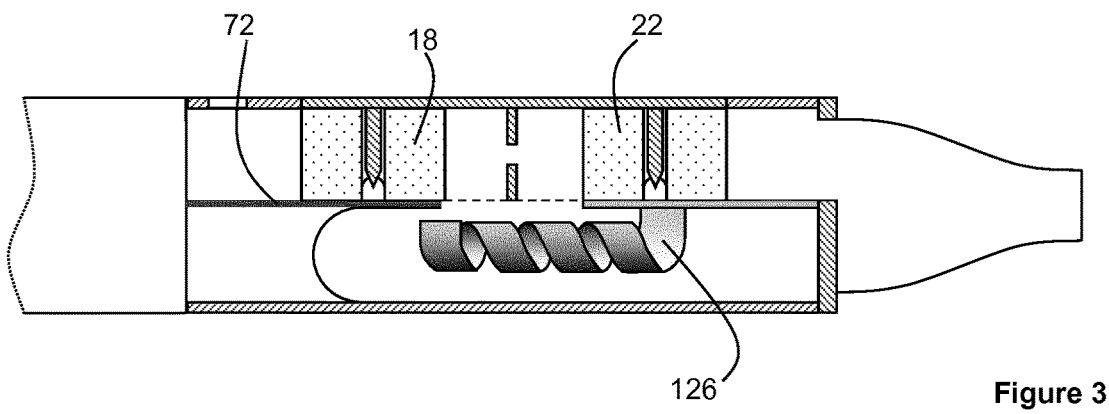
FIG. 3 shows the aerosol-generating system of FIG. 2 after the volatile delivery enhancing compound source has been heated to a predetermined temperature.

FIGS. 1, 2 and 3 show an aerosol-generating system 100 in accordance with an embodiment of the present invention. The aerosol-generating system 100 comprises an aerosol-generating article 102 in combination with an aerosol-generating device 70. The aerosol-generating device 70 comprises a heater element 72 in the form of a heater blade. The heater element 72 is electrically heated and the aerosol-generating device 70 may comprise a power source and control electronics, as is known in the art.

The aerosol-generating article 102 comprises a consumable portion 104 and a reusable portion 106 that attaches to the aerosol-generating device 70. The consumable portion 104 comprises a medicament blister 108 and a volatile delivery enhancing compound blister 110. The medicament blister 108 comprises a blister containing a liquid medicament, such as nicotine. The blister forms a frangible barrier sealing the medicament and is formed from a non-permeable material, such as a plastic. Similarly, the volatile delivery enhancing compound blister 110 comprises a blister containing a liquid volatile delivery enhancing compound, such as pyruvic acid. The blister forms a frangible barrier sealing the volatile delivery enhancing compound and is formed from a non-permeable material, such as a plastic.

The medicament blister 108 and the volatile delivery enhancing compound blister 110 are each mounted on a base plate 112 and 113 and each contained within a channel in a compressible sorption element 114. A top plate 116 overlies the sorption elements 114 and comprises side walls that extend downwardly and overlap similar side walls extending upwardly from each base plate 112 and 113. A captive mechanism, such as overlapping flanges on the side walls of the top plate 116 and each base plate 112 and 113, prevents the top plate 116 and the base plates 112 and 113 from becoming detached from each other. An overwrap 117 wraps around the top, sides and bottom of the consumable portion 104 to define an airflow passage between the upstream and downstream ends of the consumable portion 104.

First and second piercing elements 118 and 120 extend from an inner surface of the top plate 116 and overlie the medicament blister 108 and the volatile delivery enhancing compound blister 110 respectively. A restriction plate 119 comprising an airflow aperture 121 also extends from the inner surface of the top plate 116. To activate the consumable portion 104, a user depresses the top plate 116 towards the base plates 112 and 113 to compress the sorption elements 114 and to pierce the medicament blister 108 and the volatile delivery enhancing compound blister 110 with the first and second piercing elements 118 and 120. Upon piercing the blisters, the medicament and the volatile delivery enhancing compound are released and are at least partially sorbed onto the sorption elements 114 so that the sorption elements form a medicament source 18 and a volatile delivery enhancing compound source 22.

To prevent accidental activation of the consumable portion 104, the consumable portion 104 may comprise one or more resilient biasing elements, such as one or more springs, positioned between the top plate 116 and the base plates 112 and 113 to bias the top plate 116 away from the base plates 112 and 113. Additionally, or alternatively, the consumable portion 104 may comprise one or more elements that function to retain the top plate 116 and the base plates 112 and 113 in the activated position after the consumable portion 104 has been activated. For example, an interference fit between a portion of the top plate 116 and a portion of each base plate 112 and 113 may retain the top plate 116 and the base plates 112 and 113 in the activated position after the consumable portion 104 has been activated.

The reusable portion 106 comprises an outer housing 122 and a mouthpiece 44 at a downstream end of the outer housing 122. The mouthpiece 44 may be formed integrally with the outer housing 122, or the mouthpiece 44 may be formed separately and attached to the outer housing 122. An airflow inlet 124 at the upstream end of the outer housing 122 establishes an airflow passage through the outer housing 122 from the airflow inlet 124 to the mouthpiece 44.

A bimetallic strip 126 in the form of a bimetallic helix is secured at its downstream end to a thermally conductive element 128. An upstream end of the bimetallic strip 126 is resiliently biased against the heater element 72 of the aerosol-generating device 70 when the heater element 72 is inserted into the reusable portion 106, as shown in FIG. 2. To ensure correct and optimum contact between the heater element 72 and the upstream end of the bimetallic strip 126, a resilient contact spring 130 may be positioned adjacent the upstream end of the bimetallic strip 126. Although the bimetallic strip 126 is illustrated as having a helical shape, other shapes could also be used. For example, a simple flat bimetallic strip can be attached at its downstream end to the thermally conductive element 128 to form a bimetallic cantilever.

To prepare the aerosol-generating system 100 for operation, the consumable portion 104 is inserted into the reusable portion 106 through an aperture in a sidewall of the outer housing 122. Pushing the consumable portion 104 into the reusable portion 106 brings the base plate 112 into contact with the heater element 72 and brings the base plate 113 into contact with the thermally conductive element 128, as shown in FIG. 2. The consumable portion 104 may be pre-activated by the user, or the action of pushing the consumable portion 104 into the reusable portion may activate the consumable portion 104.

During operation of the aerosol-generating system 100, the heater element 72 heats the medicament source 18 via the base plate 112 and heats the volatile delivery enhancing compound source 22 via the bimetallic strip 126, the thermally conductive element 128 and the base plate 113. For this reason, the base plates 112 and 113 are constructed from a thermally conductive material, such as a metal. The bimetallic strip 126 is configured, through appropriate choice of the metals forming the strip and the shape of the strip, to undergo mechanical displacement of the upstream end of the bimetallic strip 126 away from the heater element 72 when a predetermined temperature is reached, as shown in FIG. 3. Once the predetermined temperature is reached, the upstream end of the bimetallic strip 126 no longer contacts the heater element 72, so that the volatile delivery enhancing compound source 22 is no longer heated. As the bimetallic strip 126 cools again it returns to its pre-heating shape and position so that its upstream end re-contacts the heater element 72. In this way, the bimetallic strip 126 provides thermostatic control of the heating of the volatile delivery enhancing compound source 22. By appropriate selection of the predetermined temperature at which the switching of the bimetallic strip 126 occurs, the heater element 72 heats the medicament source 18 to a higher temperature than the volatile delivery enhancing compound source 22.

The invention claimed is:

1. An aerosol-generating system, comprising:
   an aerosol-generating device comprising a heater element;
   an aerosol-generating article comprising:
      a medicament source, and
      a volatile delivery enhancing compound source; and
   a bimetallic strip provided in the aerosol-generating device or the aerosol-generating article, the bimetallic strip comprising a first end in thermal contact with the heater element and a second end in thermal contact with the volatile delivery enhancing compound source,
   wherein the bimetallic strip is configured so that heating the first end of the bimetallic strip above a predetermined temperature results in displacement of the first end of the bimetallic strip away from the heater element.

2. The aerosol-generating system according to claim 1, wherein the bimetallic strip has a helical shape, and wherein the first end of the bimetallic strip forms a first end of the helical shape and the second end of the bimetallic strip forms a second end of the helical shape.

3. The aerosol-generating system according to claim 1, wherein the bimetallic strip further comprises a first metallic layer comprising steel and a second metallic layer comprising copper or brass.

4. The aerosol-generating system according to claim 1, wherein the bimetallic strip is configured to mechanically displace the first end of the bimetallic strip away from the heater element when the first end of the bimetallic strip is heated to a temperature of at least 300 degrees Celsius.

5. The aerosol-generating system according to claim 1, wherein the volatile delivery enhancing compound source is disposed downstream of the heater element, and wherein the bimetallic strip extends between the heater element and the volatile delivery enhancing compound source.

6. The aerosol-generating system according to claim 1, wherein the aerosol-generating system is configured to heat the medicament source and the volatile delivery enhancing compound source of the aerosol-generating article so that the medicament source has a higher temperature than the volatile delivery enhancing compound source.

7. The aerosol-generating system according to claim 1, wherein the medicament source contacts the heater element.

8. The aerosol-generating system according to claim 1, wherein the aerosol-generating device and the aerosol-generating article are configured to heat the medicament source to a temperature of between 50 degrees Celsius and 150 degrees Celsius.

9. The aerosol-generating system according to claim 1, wherein the aerosol-generating device and the aerosol-generating article are configured to heat the volatile delivery enhancing compound source to a temperature of between 30 degrees Celsius and 100 degrees Celsius.

10. The aerosol-generating system according to claim 1, wherein the medicament source comprises a nicotine source.

11. The aerosol-generating system according to claim 1, wherein the volatile delivery enhancing compound source comprises an acid.

\* \* \* \* \*